(12) United States Patent
Mishkin et al.

(10) Patent No.: US 6,867,000 B2
(45) Date of Patent: Mar. 15, 2005

(54) METHOD OF ENHANCING IMMUNE RESPONSES TO HERPES

(75) Inventors: Eric M. Mishkin, Monroe, NY (US); Robert J. Natuk, Raritan, NJ (US); Michael W. Pride, Staten Island, NY (US); Maninder K. Sidhu, New City, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 77 days.

(21) Appl. No.: 10/169,057

(22) PCT Filed: Dec. 7, 2000

(86) PCT No.: PCT/US00/33105

§ 371 (c)(1), (2), (4) Date: Dec. 9, 2002

(87) PCT Pub. No.: WO01/44477

PCT Pub. Date: Jun. 21, 2001

(65) Prior Publication Data

US 2004/0067484 A1 Apr. 8, 2004

(51) Int. Cl.[7] .................................................. C12Q 1/68
(52) U.S. Cl. ........................ 435/6; 435/69.1; 424/229.1; 424/278.1
(58) Field of Search ........................... 424/229.1, 278.1, 424/204.1, 199.1; 435/6, 69.1, 320.1

(56) References Cited

U.S. PATENT DOCUMENTS 5,958,895 A * 9/1999 Pachuk et al. ................. 514/44
6,235,290 B1 * 5/2001 Brunham .................. 424/263.1

FOREIGN PATENT DOCUMENTS

| WO | WO 9603510 A1 * | 2/1996 |
| WO | WO99/40938 A2 | 8/1999 |

OTHER PUBLICATIONS

Sin, Jeong–Im, et al., In Vivo Modulation of Vaccine–Induced Immune Responses toward a Th1 Phenotype Increases Potency and Vaccine Effectiveness in a Herpes Simplex Virus Type 2 Mouse Model, Journal of Virology, Jan. 1999, 501–509, 73:1.

Sin, Jeong–Im, et al., IL–12 Gene as a DNA Vaccine Adjuvant in a Herpes Mouse Model: IL–12 Enhances Th1–Type CD4+ T Cell–Mediated Protective Immunity Against Herpes Simplex Virus–2 Challenge, The Journal of Immunology, 1999, 2912–2921, 162.

Sin, Jeong–Im, Et Al., DNA Priming–Protein Boosting Enhances Both Antigen–Specific Antibody and Th1–Type Cellular Immune Responses in a Murine Herpes Simplex Virus–2 gD Vaccine Model, DNA and Cell Biology, Oct. 1999, 771–779, 18:10.

Bernstein, D. I., Et Al., Effects of DNA Immunization Formulated with Bupivacaine in Murine and Guinea Pig Models of Genital Herpes Simplex Virus Infection, Vaccine, Apr. 9, 1999, 1964–1969, 17:15–16.

* cited by examiner

*Primary Examiner*—Ali R. Salimi
(74) *Attorney, Agent, or Firm*—Bill T. Brazil

(57) ABSTRACT

A method for inducing and enhancing protective and/or therapeutic immunity in a mammal to HSV includes the steps of at least one immunization with an effective amount of a DNA vaccine composition which comprises a first nucleic acid molecule comprising a DNA sequence encoding the HSV type 1 or type 2 gD protein, and a second nucleic acid molecule comprising a DNA sequence encoding each Interleukin-12 heterodimer subunit. The method also comprises at least one subsequent immunization with an effective amount of a protein vaccine composition which comprises the HSV type 1 or type 2 gD protein; and the IL-12 heterodimer. A local anesthetic may be included in the DNA vaccine composition in an amount that forms one or more complexes with the nucleic acid molecules. When provided to the mammal in suitable effective dosages according to this protocol, the vaccine compositions used in this method produce an unexpectedly good protective and/or therapeutic immune response against HSV in an immunized mammal.

12 Claims, 1 Drawing Sheet

METHOD OF ENHANCING IMMUNE RESPONSES TO HERPES

FIELD OF THE INVENTION

The invention relates generally to the field of vaccines, and more specifically to a vaccine regimen for inducing immunity against Herpes Simplex virus that employs both a nucleic acid vaccine and a protein vaccine, with a selected adjuvant.

BACKGROUND OF THE INVENTION

A variety of vaccine formulations exist for inducing immune responses to certain pathogens, such as Herpes Simplex Virus (HSV). A focus of HSV vaccines has been the HSV type 1 and HSV type 2, glycoprotein D (gD) genes. See, G. H. Cohen et al, *J. Virol.*, 62(8):1932–1940 (1988); H-Y. Chiang et al, *J. Virol.*, 68(4):2529–2543 (1994); A. V. Nicola et al, *J. Virol*, 70(6):3815–3822 (1996); and U.S. Pat. No. 5,654,174.

Known formulations for vaccines have employed a variety of delivery vehicles for presenting such antigens as the gD gene to the mammalian immune system, so as to invoke a protective immune response against the pathogen. Such "delivery vehicles" have included as a vaccine agent heat or chemically-inactivated whole virus, protein particles of the whole virus, virus vectors, such as adenovirus and vaccinia, among others, and DNA-based vectors or plasmids. An example of the latter type of formulation for the HSV gD gene is taught in International patent application No. WO98/17820, published on Apr. 30, 1998 and U.S. Pat. No. 5,958,895. Alternatively, other delivery agents may be additives to, e.g., the plasmid based vehicles, which aid in the delivery or presentation of the antigen to the immune system. See, e.g., International patent application No. WO98/48780, published Nov. 5, 1998.

Still other variations on vaccines for a wide number of pathogens include compositions and formulations containing other agents for delivery with the antigen against which an immune response is desired. These other agents may be of the type which increase or enhance the immune response to the antigen by their own bioactivity. For example, certain cytokines and interleukins have been found to be desirable "adjuvants" for vaccine compositions. Among the more interesting of these is Interleukin-12. See, e.g., U.S. Pat. Nos. 5,723,127 and 5,571,515.

As yet another means to obtain a suitably protective immune response to any number of vaccines against pathogens, various protocols for vaccination have been proposed. For example, prior studies have demonstrated that plasmid-based vaccines can be employed to prime the immune system to a second immunization with a another form of the same antigen, such as a protein or a recombinant virus [S. W. Barnett et al, *Vaccine*, 15 (80):869–873 (1997); N. L. Letvin et al, *Proc. Natl. Acad. Sci. USA* 94:9378–9383 (1997); R. A Gramzinski et al, *Molecular Med.*, 4:109–118 (1998); J. Schneider et al, *Nature Med.*, 4:397 (1998); and M. Sedeguh et al., *Proc. Natl. Acad. Sci. USA*, 95:7648 (1998)].

Despite the wealth of information on vaccines and vaccine formulations, there continues to be a need for efficacious vaccines to induce or confer adequate protective immunity in humans to HSV, in particular.

SUMMARY OF THE INVENTION

In one aspect, the invention relates to a method of inducing mammalian immunity to a Herpes Simplex Virus pathogen. The method includes the step of: administering an effective amount of a vaccine composition which comprises, a first vaccine which comprises a nucleic acid molecule comprising a DNA sequence encoding the HSV type 1 or type 2 gD protein and a second nucleic acid molecule comprising a DNA sequence encoding the Interleukin-12 p-35 and p40 heterodimeric subunits. Preferably the second nucleic acid molecule comprises an equal mixture of a nucleic acid molecule comprising a DNA sequence encoding IL-12 p35 and nucleic acid molecule comprising a DNA sequence encoding IL-12 p40.

After at least one immunization of a mammal with this DNA vaccine, the method further includes at least one immunization of the mammal with an effective amount of a second vaccine composition which comprises a protein, in particular, the HSV type 1 or type 2 gD protein, and the IL-12 heterodimer proteins in a suitable pharmaceutical carrier. In an optional embodiment, the first vaccine is administered in a formulation with a local anesthetic in an amount that forms one or more complexes with the nucleic acid molecules of the first vaccine.

In yet another aspect, this invention includes an HSV vaccine kit which contains the various components itemized above in the vaccine method, as well as instructions and optional apparatus suitable for mixing and administering the vaccine components.

Other aspects and advantages of the present invention are described further in the following detailed description of the preferred embodiments thereof.

Figure 1:
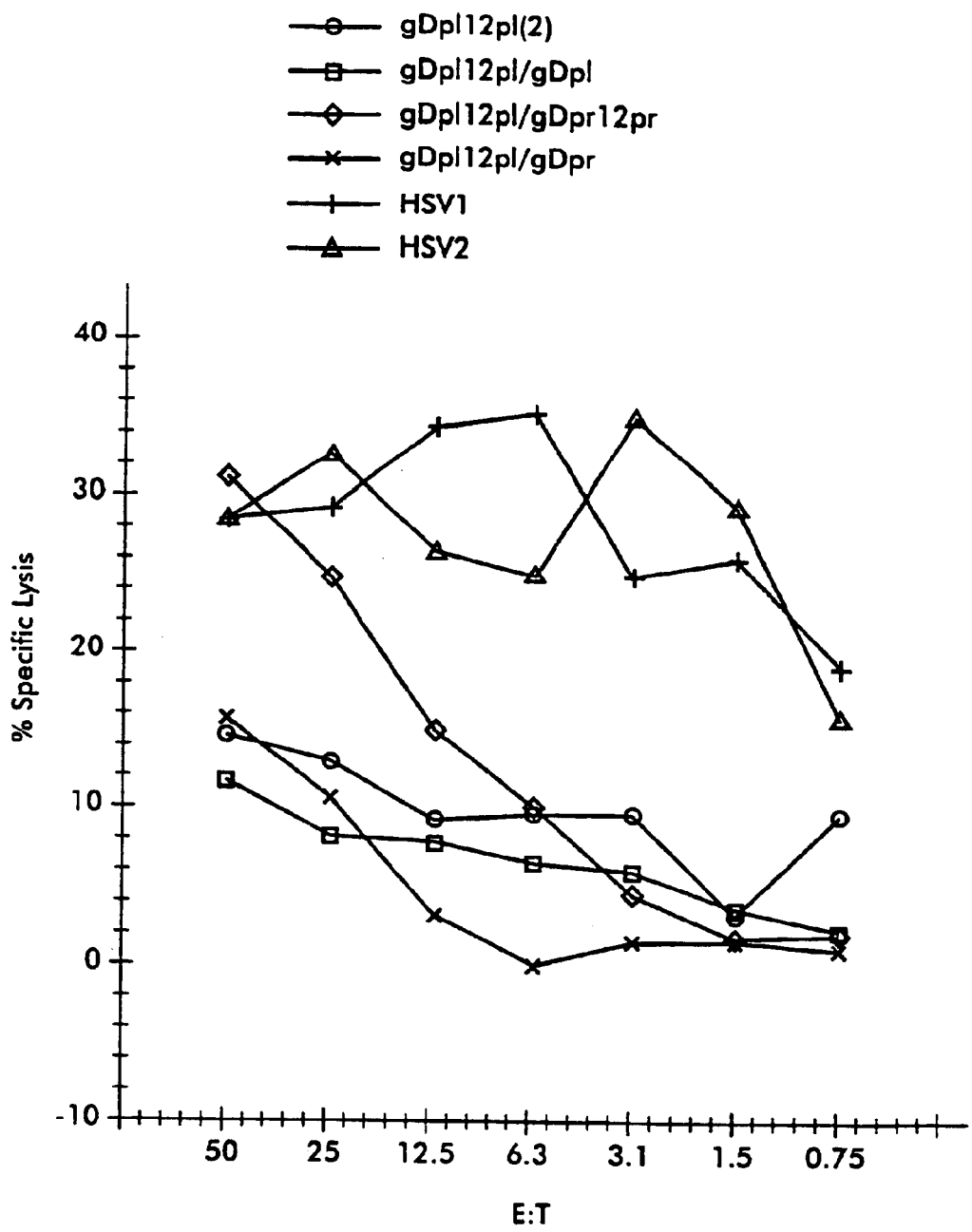
FIG. 1 is a graph illustrating the cytotoxic T lymphocyte (CTL) activity for the experimental animals of the assay described in Example 2. The graph plots % specific lysis vs. effector:target ratio. The following symbols represent the following experimental groups.

"○" represents animals receiving two identical immunizations with the "first" vaccine containing a DNA plasmid encoding the HSV gD2 gene and the DNA plasmids encoding the two heterodimers of IL-12 (gDpl12pl);

"□" represents animals receiving one immunization with the "first" vaccine described above followed by one immunization with the DNA plasmid encoding the HSV gD2 gene alone (gDpl12pl/gDpl);

"◇" represents animals receiving the "first" vaccine (gDpl12pl) followed by one immunization with the "second" vaccine containing a gD subunit protein and the IL-12 heterodimeric protein (gDpr12pr);

"X" represents animals receiving the first vaccine (gdpl12pl), followed by one immunization with the gD subunit protein alone (gDpr);

"+" represents control animals receiving only the live virus HSV1; and

"Δ" represents control animals receiving only the live virus HSV2.

DETAILED DESCRIPTION OF THE INVENTION

The present invention provides an effective vaccine protocol for the prevention or treatment of infection of mammals by Herpes Simplex virus. This vaccine method, which involves a prime-boost immunization, induces protective and/or therapeutic immunity in a mammal to the pathogen, Herpes Simplex Virus, type 1 or type 2. The present invention demonstrates that a prime-boost vaccine regimen, in which the HSV gD is administered at the DNA priming stage, the optional DNA boosting stage, and the protein boosting stage with IL-12 in the same form as the gD, augments cell-mediated immunity, which is considered crucial for therapy. The broad spectrum of immunity demonstrated by this regimen also provides enhanced protective and/or therapeutic immunity against HSV infection. Thus, this invention provides a method useful for both prophylaxis and therapy of HSV infection, e.g., for pre-exposed and post-exposed subjects.

I. Definitions

The terms "mammal" and "mammalian" are intended to encompass their normal meaning. While the invention is most desirably intended for efficacy in humans, other primates as well as domestic mammalian species, including without limitation, dogs, cats, cows, horses, pigs, sheep, goats, mice, rabbits, and rats, etc. are also encompassed by this definition.

By "immune response" or "immunity" as the terms are interchangeably used herein, is meant the induction of a humoral (i.e., B cell) and/or cellular (i.e., T cell) response. Suitably, a humoral immune response may be assessed by measuring the antigen-specific antibodies present in serum of immunized animals in response to introduction of the HSV gD antigen into the host. In one exemplary embodiment below, the immune response is assessed by the enzyme linked immunosorbant assay of sera of immunized mammals, or by microneutralization assay of immunized animal sera, as discussed in Example 2 below. A CTL assay can be employed to measure the T cell response from lymphocytes isolated from the spleen of immunized animals, also as described below.

The terms "prime" and "boost" are intended to have their ordinary meanings in the art. "Priming" refers to immunizing with a first composition, which induces a higher level of immune response to the antigen upon subsequent immunization ("Boosting") with the same or another composition, than the immune response obtained by immunization with a single vaccine composition, e.g., the priming composition alone or the boosting composition alone.

The term "homologous" as used herein, refers to the sequence similarity between two polymeric molecules, e.g., between two nucleic acid molecules, e.g., two DNA molecules or two RNA molecules, or between two polypeptide molecules. When a nucleotide or amino acid position in both of the two molecules is occupied by the same monomeric nucleotide or amino acid, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology. By the term "substantially homologous" as used herein, is meant DNA or RNA which is about 50% homologous, more preferably about 70% homologous, even more preferably about 80% homologous and most preferably about 90% homologous to the desired nucleic acid.

Where as discussed herein, HSV gD or IL-12 protein and/or DNA sequences are defined by their percent homologies or identities to identified sequences, the algorithms used to calculate the percent homologies or percent identities include the following: the Smith-Waterman algorithm [J. F. Collins et al, 1988, Comput. Appl. Biosci., 4:67–72; J. F. Collins et al, Molecular Sequence Comparison and Alignment, (M. J. Bishop et al, eds.) In Practical Approach Series: Nucleic Acid and Protein Sequence Analysis XVIII, IRL Press: Oxford, England, UK (1987) pp.417], and the BLAST and FASTA programs [E. G. Shpaer et al, 1996, Genomics 38: 179–191]. These references are incorporated herein by reference.

II. Priming with gD and IL-12 DNA

According to this invention, the first or priming step of the method involves immunizing a mammal with an effective amount of a first "priming" vaccine containing a first nucleic acid molecule comprising a DNA sequence encoding the HSV type 1 or type 2 gD protein in combination with a second nucleic acid molecule comprising a DNA sequence encoding each subunit of the Interleukin-12 heterodimer. This second nucleic acid sequence can encompass a mixture of two separate nucleic acid molecules, each encoding a different IL-12 heterodimer, or can be a bicistronic molecule containing both heterodimeric subunits, or a single sequence of the IL-12 subunits or biologically active fragments thereof linked or fused together in a single molecule. The sequences encoding the gD1 and gD2 proteins are known (see, e.g., GenBank Accession No. K01408 and references cited in the background above) and those of the IL-12 heterodimers are also known (see, e.g., U.S. Pat. No. 5,457,038).

Preferably, the native HSV gD1 or gD2 sequence is used in the priming vaccine; however, the invention contemplates the use of modified sequences of gD1 and gD2, where such modification of the nucleic acid sequences enhances the immunogenicity, stability, or some other pharmacological property of the gD genes in vivo. Numerous nucleotide sequence modifications are known and are discussed in general below. Among such modifications are included truncations or deletions/insertions to shorten or lengthen the native gD sequence. The gD sequence may be truncated at its 5' end to remove a signal or leader sequence. Alternatively, the gD sequence may be truncated at its 3' end to remove its transmembrane domain or its cysteine-rich region. Still another alternative is a gD molecule truncated at both 5' and 3' ends to remove both the signal and transmembrane domains. Still another example of a modified gD gene is a sequence with the native leader or signal sequence deleted and replaced by another signal sequence. For example, the sequence may be truncated at the codon encoding the amino acid at residue 285 or residue 316 of gD to provide a modified gD sequence useful in this invention. Still other modifications are likely to be useful (see, e.g., the fragments described in U.S. Pat. No. 5,958,895).

The present invention also includes nucleic acid sequences encoding gD which are fused in the same reading frame to a another polynucleotide sequence which aids in expression and secretion of a polypeptide from the immunized host's cell or which aids in the stability of the polypeptide in a cell, for example, a leader sequence which functions as a secretory sequence for controlling transport of a polypeptide from the cell.

Similarly, the sequences of the IL-12 p35 and p40 heterodimeric subunits of several mammalian species, including murine and human, are known in the art. Preferably the selected IL-12 subunit sequence employed is a native or allelic sequence of the mammalian species being administered the priming vaccine. For example, most preferred for use in human subjects is the native human IL-12 heterodimer. Further, the invention contemplates the use of modified sequences of IL 12 p35 and IL-12 p40, where such modification of the nucleic acid sequences enhances the stability or some other pharmacological property of the IL-12 subunit genes in vivo. For example, a single gene could be designed which contains both heterodimers or the biologically relevant fragments of both heterodimers linked together. Numerous nucleotide sequence modifications are known and are discussed in general below.

Nucleotide sequences encoding HSV gD or encoding the IL-12 heterodimer which have sequences which are respectively homologous with the gD antigen's or IL-12 cytokine's amino acid sequence, where the homologous antigen induces an immune response to HSV or an appropriate response to IL-12, are also useful in the priming vaccine and boosting vaccine of the method of this invention. Genes which are homologous to the desired gD-encoding sequence should be construed to be included in the invention provided they encode a protein or polypeptide which can induce a protective immune response against HSV substantially similar to that of the native or wild-type HSV gD.

Methods for preparing the components of the priming vaccine step of the invention are described in conventional texts, such as Burger et al., *J. Gen. Virol.*, 72:359–367 (1991), and are well-known in the art. See also Sambrook et al., 1989, *Molecular Cloning: A Laboratory Manual*, Cold Spring Harbor Laboratory Press, New York; and Ausubel et al., 1997, *Current Protocols in Molecular Biology*, Green & Wiley, New York. Alternatively, suitable plasmids containing an HSV gD nucleic acid sequence or IL-12 subunit nucleic acid molecules may be purchased commercially.

Each nucleic acid sequence encoding gD, IL-12 p35, or IL-12 p40 is preferably under the control of regulatory sequences that direct the replication and generation of the product of each nucleic acid sequence in a mammalian cell. By the term "promoter/regulatory sequence" is meant a DNA sequence which is required f r expression of a nucleic acid operably linked to the promoter/regulatory sequence. In some instances, the promoter/regulatory sequence may function in a tissue specific manner, in that, the promoter/regulatory sequence is only capable of driving expression in a cell of a particular tissue type. In some instances, this sequence may be the core promoter sequence and in other instances, this sequence may also include an enhancer sequence and other regulatory elements which are required for expression in a tissue-specific manner.

By describing two DNAs as being "operably linked" as used herein, is meant that a single-stranded or double-stranded DNA comprises each of the two DNAs and that the two DNAs are arranged within the DNA in such a manner that at least one of the DNA sequences is able to exert a physiological effect by which it is characterized upon the other. Preferably, when the nucleic acid encoding gD or IL-12 further comprises a promoter/regulatory sequence, the promoter/regulatory sequence is positioned at the 5' end of the coding sequence such that it drives expression of the gD or IL-12 in a cell.

Such regulatory sequences include, without limitation, a promoter sequence, an enhancer sequence, a polyadenylation sequence, a splice donor sequence and a splice acceptor sequence. The art provides a wealth of such sequences from which to design the DNA molecules useful in this invention. One of skill in the art may readily select from among such known regulatory sequences to prepare molecules of this invention and the selection of such regulatory sequences is not a limitation of this invention. For example, the promoters employed in the plasmids or other DNA molecules which are part of the priming vaccine may include constitutive promoters which are non-specific in activity. Such promoters include, without limitation, the retroviral LTR promoter, the cytomegalovirus (CMV) immediate early promoter, the SV40 promoter, the dihydrofolate reductase promoter, and the phosphoglycerol kinase (PGK) promoter. Inducible promoters which are regulated by exogenously applied drugs, may also be employed. These include, without limitation, the zinc-inducible sheep metallothionine (MT) promoter, and the dexamethasone (Dex)-inducible mouse mammary tumor virus (MMTV) promoter, among others. Other types of inducible promoters which may be useful in this context are those which are regulated by a specific physiological state, e.g., temperature or acute phase or in replicating cells only.

Preferably, the nucleic acid sequences encoding gD or IL-12 heterodimers are administered in a vector or plasmid. By the term "vector" as used herein, is meant a DNA molecule derived from viral or bacterial species which has been designed to encode an exogenous or heterologous nucleic acid sequence. Thus, the term includes conventional bacterial plasmids. Such plasmids or vectors can include plasmid sequences from viruses or phages. Such vectors include chromosomal, episomal and virus-derived vectors e.g., vectors derived from bacterial plasmids, bacteriophages, yeast episomes, yeast chromosomal elements, and viruses, vectors derived from combinations thereof such as those derived from plasmid and bacteriophage genetic elements, cosmids and phagemids. The term also includes non-replicating viruses which transfer a gene from one cell to another. The term should also be construed to include non-plasmid and non-viral compounds which facilitate transfer of nucleic acid into cells, such as, for example, polylysine compounds and the like. Examples of viral vectors include, but are not limited to, adenoviral vectors, poxvirus vectors, retroviral vectors, and the like. Examples of bacterial vectors include, but are not limited to, sequences derived from bacille Calmette Guérin (BCG), Salmonella, Shigella, and Listeria, among others. Thus, one exemplary vector is a single or double-stranded phage vector. Another exemplary vector is a single or double-stranded RNA or DNA viral vector.

In addition to the regulatory sequences mentioned above, plasmids may contain sites for transcription initiation and termination, and, in the transcribed region, a ribosome binding site for translation. The coding portion of the mature transcripts expressed by the constructs will include a translation initiating codon at the beginning and a termination codon appropriately positioned at the end of the polypeptide to be translated.

All components of the plasmids or vectors above may be readily selected from among known materials in the art and available from the pharmaceutical industry. Selection of the plasmid backbone and regulatory sequences are not considered a limitation on this invention.

Preferably, for use in the priming vaccine step of this invention, the gD gene and each IL-12 subunit is present in a separate plasmid. Alternatively, two or more of these nucleic acid sequences may be contained in a polycistronic transcript, i.e., a single molecule which is designed to express two of the three, or all three, gene products.

The priming vaccine thus contains one or more of the nucleic acid sequences encoding HSV gD and the IL-12 heterodimer in a suitable pharmaceutically-, or physiologically acceptable carrier, such as isotonic saline or isotonic salts solution. The appropriate carrier will be evident to those skilled in the art and will depend in large part upon the route of administration. Alternatively, such priming vaccines composed of polynucleotide molecules desirably contain optional polynucleotide facilitating agents or "co-agents", such as a local anaesthetic, a peptide, a lipid including cationic lipids, a liposome or lipidic particle, a polycation such as polylysine, a branched, three-dimensional polycation such as a dendrimer, a carbohydrate, a cationic amphiphile, a detergent, a benzylammonium surfactant, or another compound that facilitates polynucleotide transfer to cells. Non-exclusive examples of such facilitating agents or co-agents useful in this invention are described in U.S. Pat. Nos. 5,593,972; 5,703,055; 5,739,118; 5,837,533; International Patent Application No. WO96/10038, published Apr. 4, 1996; and International Patent Application No WO94/16737, published Aug. 8, 1994, which are each incorporated herein by reference.

Most preferably, the local anesthetic is present in an amount that forms one or more complexes with the nucleic acid molecules. When the local anesthetic is mixed with the DNA plasmids, it forms a variety of small complexes or particles which pack the DNA and are homogeneous. Thus, in one embodiment of the priming vaccine compositions of this invention, the complexes are formed by mixing the local anesthetic and from one to three of the DNA plasmids (the two IL-12 subunit-containing plasmids, or the gD-containing plasmid and one or both of the IL-12 subunit-containing plasmids, or the gD-containing plasmid and a bicistronic plasmid containing both the IL-12 subunits, or a single polycistronic plasmid containing the gD sequence and both IL-12 subunit sequences). Any single complex resulting from this mixture may contain a variety of combinations of the different plasmids. Alternatively, in another embodiment of the priming compositions of this invention, the local anesthetic may be pre-mixed with each gD and IL-12 subunit plasmid separately, and then the separate mixtures combined in a single priming composition to ensure the desired ratio of the plasmids is present in a single vaccine composition, if all plasmids are to be administered in a single bolus administration. Alternatively, the local anesthetic and each plasmid may be mixed separately and administered separately to obtain the desired ratio. Where, hereafter, the term "complex" or "one or more complexes" or "complexes" is used to define this embodiment of the priming vaccine composition, it is understood that the term encompasses one or more complexes with each complex containing a mixture of the gD and IL-12 subunit-containing plasmids, or a mixture of complexes formed discretely, wherein each complex contains only one type of plasmid, or a one or a mixture of complexes wherein each complex contains a polycistronic DNA.

Preferably, the complexes are between about 50 to about 150 nm in diameter. When the facilitating agent used is a local anesthetic, preferably bupivacaine, an amount of from about 0.1 weight percent to about 1.0 weight percent based on the total weight of the polynucleotide composition is preferred. See, also, International Patent Application No. PCT/US98/22841, which is hereby incorporated by reference, and which teaches the incorporation of benzylammonium surfactants as co-agents, preferably administered in an amount of between about 0.001–0.03 weight %. According to the present invention, the amount of local anesthetic is present in a ratio to said nucleic acid molecules of 0.01–2.5% w/v local anesthetic to 1–10 $\mu$g/ml nucleic acid. Another such range is 0.05–1.25% w/v local anesthetic to 100 $\mu$g/ml to 1 ml/ml nucleic acid.

The pharmaceutical compositions may also contain other additives suitable for the selected mode of administration of the composition. The composition of the invention may also involve lyophilized polynucleotides, which can be used with other pharmaceutically acceptable excipients for developing powder, liquid or suspension dosage forms. See, e.g., Remington: The Science and Practice of Pharmacy, Vol. 2, $19^{th}$ edition (1995), e.g., Chapter 95 Aerosols; and International Patent Application No. PCT/US99/05547, the teachings of which are hereby incorporated by reference. Routes of administration for these compositions may be combined, if desired, or adjusted.

Thus, these priming/DNA boosting vaccine compositions can contain additives suitable for administration via any conventional route of administration. In some preferred embodiments, the priming composition and optional DNA boosting composition of the invention are prepared for administration to mammalian subjects in the form of for example, liquids, powders, aerosols, tablets, capsules, enteric coated tablets or capsules, or suppositories. Routes of administration include, without limitation, parenteral administration, intraperitoneal administration, intravenous administration, intramuscular administration, subcutaneous administration, intradermal administration, oral administration, topical administration, intranasal administration, intra-pulmonary administration, rectal administration, vaginal administration, and the like. All such routes are suitable for administration of these compositions, and may be selected depending on the patient and condition treated, and similar factors by an attending physician.

In general, selection of the appropriate dosage for the priming compositions of the present invention will be based upon the physical condition of the mammal, most especially including the general health and weight of the immunized mammal. Such selection and upward or downward adjustment of the effective dose is within the skill of the art.

In the methods of the examples below, the components of the priming vaccines were co-administered to the mammal. The nucleic acid molecules containing the gD gene, and each IL-12 subunit were first mixed in a suitable pharmaceutical carrier and then administered together as a single bolus.

Alternatively, it is contemplated that each plasmid may be administered separately and sequentially. As an illustrative priming vaccine step, the following examples demonstrate delivery of the three bacterial plasmids, pMVgD2, pMVp35 and pMVp40, admixed and administered in saline intramuscularly. Other administrations may be contemplated.

III. The Optional Nucleic Acid Boost

The method of this invention further contemplates an optional boosting vaccine comprising the same components and formulation as described for the "priming vaccine" above. This nucleic acid boost is desirably administered to the patient about 4 weeks to about 32 weeks following the administration of the priming vaccine. Desirably, the nucleic acid boost is administered via the same route and at the same dosages as provided for the priming vaccine step described above.

IV. The HSV gD and IL-12 Heterodimer Protein Boost

Further provided by the method of this invention is a protein boosting vaccine step. This step of the method preferably involves immunizing the mammal with an effective amount of a protein vaccine composition, which comprises the HSV type 1 or type 2 gD protein or an analog thereof and the IL-12 heterodimer or an analog thereof between about 2 weeks to 32 weeks following immunization with the "priming vaccine" described above or following immunization with one or more optional nucleic acid boosts described above.

As mentioned above the DNA and protein sequences of HSV gD, types 1 and 2, and the murine and human IL-12 heterodimeric subunits are well known in the art. The term "analog" when referring to the gD or IL-12 polypeptide useful in this invention, means a full-length polypeptide or a fragment thereof which retains essentially the same biological function or activity as such polypeptide, i.e., functions as an immunogen. The analog of the gD and/or IL-12 heterodimer polypeptide may be (i) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; (ii) one in which the polypeptide is fused with another compound, such as a compound to increase the half-life of the polypeptide (for example, polyethylene glycol); or (iv) one in which the additional amino acids are fused to the polypeptide, such as a leader or secretory sequence or a sequence which is employed for purification of the polypeptide. Such analogs are deemed to be within the scope of those skilled in the art from the teachings herein. Analogs of HSV gD or the IL-12 heterodimers described herein can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function.

Modifications (which do not normally alter primary sequence) include in vivo, or in vitro chemical derivatization of polypeptides, e.g., acetylation, or carboxylation. Also included as analogs of gD or IL-12 are these proteins modified by glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced as analogs according to this invention are HSV gD or IL-12 sequences which have phosphorylated amino acid residues, e.g., phosphotyrosine, phosphoserine, or phosphothreonine. Also included as analogs are gD or IL-12 polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. Among other known modifications which may be present in polypeptides of the present invention are, without limitation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, GPI anchor formation, hydroxylation, iodination, methylation, myristoylation, oxidation, proteolytic processing, prenylation, racemization, selenoylation, sulfation, transfer-RNA mediated addition of amino acids to proteins such as arginylation, and ubiquitination.

Still other modifications, particularly of the gD protein include the above-mentioned deletion of the signal or leader sequence at the N terminus of gD, and/or the deletion of the transmembrane domain and/or cysteine-rich region at the C terminus of gD, or both. Similarly, a modification could include replacing the signal or leader sequence with another signal or leader sequence. See, e.g., U.S. Pat. No. 5,958,895.

Methods for making such modifications are well known to those of skill. See, e.g., PROTEINS—STRUCTURE AND MOLECULAR PROPERTIES, 2nd Ed., T. E. Creighton, W. H. Freeman and Company, New York, 1993; Wold, F., "Posttranslational Protein Modifications: Perspectives and Prospects", pgs. 1–12 in POSTTRANSLATIONAL COVALENT MODIFICATION OF PROTEINS, B. C. Johnson, Ed., Academic Press, New York, 1983; Seifter et al., *Meth. Enzymol.*, 182:626–646 (1990), and Rattan et al., *Ann, N.Y. Acad, Sci.*, 663:48–62 (1992).

In addition to substantially full length polypeptides, the gD and/or IL-12 proteins useful in the present invention include immunologically active fragments of these polypeptides. As used herein, the term "fragment," as applied to a polypeptide, will ordinarily be at least about six contiguous amino acids, typically at least about 15, or about 25, contiguous amino acids, more typically at least about 40 contiguous amino acids, usually at least about 45 contiguous amino acids and preferably at least about 50 contiguous amino acids in length. See, for example, the gD polypeptides described in U.S. Pat. No. 4,709,011, which is incorporated herein by reference. The gD protein, analog or fragment thereof is useful in the present method if it induces a protective immune response to HSV type 1 or 2 in the subject mammal. For example, a gD protein truncated at about residue 285 is a desirable fragment. Similarly, a gD protein truncated at about residue 316 is a desirable fragment. Still other fragments of gD may be selected. The IL-12 protein, analog or fragment thereof is useful in the present method if it enhances the immune response induced by the gD protein.

The gD protein and IL-12 heterodimer used in the protein boosting vaccine of the invention are not limited to products of any of the specific exemplary processes listed herein. In fact, the gD protein and IL-12 heterodimer proteins may be prepared by the methods extant in the texts cited immediately above or by methods of the texts cited in the priming vaccine section above. It is within the skill of the art to isolate and produce protein compositions for vaccine use. Still alternatively, the gD and L-12 proteins may be purchased commercially.

The protein boosting compositions are desirably formulated into pharmaceutical compositions. Such formulations comprise the gD protein and the IL-12 heterodimer combined with a pharmaceutically acceptable carrier, such as sterile water or sterile isotonic saline. The appropriate carrier will be evident to those skilled in the art and will depend in large part upon the route of administration. Formulations include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Still additional components that may be present in the protein boosting compositions are adjuvants, preservatives, chemical stabilizers, or other antigenic proteins. Typically, stabilizers, adjuvants, and preservatives are optimized to determine the best formulation for efficacy in the target human or animal. Suitable exemplary preservatives include chlorobutanol potassium sorbate, sorbic acid, sulfur dioxide, propyl gallate, the parabens, ethyl vanillin, glycerin, phenol, and parachlorophenol. Suitable stabilizing ingredients which may be used include, for example, casamino acids, sucrose, gelatin, phenol red, N-Z amine, monopotassium diphosphate, lactose, lactalbumin hydrolysate, and dried milk. A conventional adjuvant is used to attract leukocytes or enhance an immune response. Such adjuvants include, among others, MPL™ (3-O-deacylated monophosphoryl lipid A; RIBI ImmunoChem Research, Inc., Hamilton, Mont.), mineral oil and water, aluminum hydroxide, Amphigen, Avridine, L121/squalene, D-lactide-polylactide/glycoside, pluronic plyois, muramyl dipeptide, killed *Bordetella*, saponins, such as Quil A or Stimulon™ QS-21 (Aquila Biopharmaceuticals, Inc., Framingham, Mass.) and cholera toxin (either in a wild-type or mutant form, e.g., wherein the glutamic acid at amino acid position 29 is replaced by another amino acid, preferably a histidine, in accordance with International Patent Application No. PCT/US99/22520, incorporated herein by reference).

In some preferred embodiments, the boosting composition of the invention is prepared for administration to mammalian subjects in the form of for example, liquids, powders, aerosols, tablets, capsules, enteric coated tablets or capsules, or suppositories. Routes of administration include, without limitation, parenteral administration, intraperitoneal administration, intravenous administration, intramuscular administration, subcutaneous administration, intradermal administration, oral administration, topical administration, intranasal administration, intra-pulmonary administration, rectal administration, vaginal administration, and the like. All such routes are suitable for administration of these compositions, and may be selected depending on the patient and condition treated, and similar factors by an attending physician.

In general, selection of the appropriate dosage of the protein boosting composition of the present invention will be based upon the physical condition of the mammal most especially including the general health and weight of the immunized mammal. Such selection of appropriate dosages per patient is within the skill of the art.

In the methods of the examples below, the components of the preferred protein boost vaccines were mixed and administered i.m. in a single injection. It is also possible that the gD protein would be administered separately from the IL-12 heterodimer, each in a suitable pharmaceutical carrier.

V. A Kit of the Invention

Also included in the invention is a kit for inducing an enhanced HSV protective and/or therapeutic immune response. Such a kit preferably comprises the components of a priming vaccine, i.e., one or more nucleic acid molecules as described above comprising a DNA sequence encoding the HSV type 1 or 2 gD gene, and a DNA sequence encoding the Interleukin-12 p-35 and p40 subunits, wherein the DNA sequence encoding the gD gene and the DNA sequence encoding said IL-12 heterodimers are each under the control of regulatory sequences directing expression thereof in a mammalian cell. Optionally the kit contains a local anesthetic in an amount that forms one or more complexes with these nucleic acid molecules. Optionally the kit contains the components of the DNA boosting vaccine, as described above. The kit also contains the components of the protein boosting vaccine, i.e., the HSV type 1 or type 2 gD protein and the IL-12 heterodimer in a pharmaceutically acceptable carrier as described above.

Other components of the kit include applicators for administering each composition. By the term "applicator" as the term is used herein, is meant any device including but not limited to a hypodermic syringe, gene gun, nebulizer, dropper, bronchoscope, suppository, among many well-known types for administration of pharmaceutical compositions useful for administering the DNA vaccine components and/or the protein vaccine components by any suitable route to the human or veterinary patient. Still another component involves instructions for using the kit.

THE EXAMPLES

The invention is further described in detail by reference to the following experimental examples. These examples are provided for purposes of illustration only, and are not intended to be limiting unless otherwise specified. The invention should not be construed as being limited to the use of the particular DNA plasmid and plasmid components, such as promoters, employed as the priming DNA vaccines, nor to the particular local anesthetic described herein. Thus, the invention encompasses any and all variations which become evident as a result of the teaching provided herein.

Example 1: The HSV Vaccine Components

A. The Priming Vaccines.

The PMV plasmid was derived from pCMV-β [Clontech, Inc.], by removing the beta-galactosidase and SV40 poly A sites and replacing the deleted sequences with bovine Growth Hormone (bGH) poly A, isolated from pcDNA3.1 [Invitrogen, Inc.]. Other features of the PMV plasmid include a pUC origin of replication, an intron containing the SV40 splice donor/acceptor and an ampicillin resistance gene. The PMVgD plasmid was constructed as follows: A 1.5 kb HindIII-BstX1 fragment containing gD gene from HSV type 2 (HSV-2) strain 186 was isolated from plasmid pww65 [Eisenberg et al, *J. Virol.*, 64:8 (1990)]. The 5' overhangs were filled with Klenow fragment, followed by cloning into the SmaI site of PMV plasmid. The resulting plasmid expresses gD2 from CMV promoter and is polyadenylated with Bovine Growth Hormone poly A.

The IL-12 heterodimer containing plasmids were PMVp35 and PMVp40, and these plasmids were constructed as follows: Mouse IL-112 cDNAs for p35 (650 bp) and p40 (1.0 kb) were isolated as individual SalI-XhoI fragments from plasmids pEDIL-12p35 and pEDIL-12p40 [both obtained from Genetics Institute, Inc., Cambridge, Mass.; see, also, S. A Wolf et al, *J. Immunol.*, 146:3074–3081 (1991)]. These fragments were cloned into the SalI-XhoI site of individual PMV plasmids, described above, generating PMVp35 and PMVp40. Each plasmid expressed the p35 or p40 IL-12 heterodimer from the cytomegalovirus promoter and contains the bovine growth hormone poly A.

As illustrated in the protocols of Examples 2 and 3 below, a preferred priming vaccine comprises 35 micrograms of each of plasmid pMVgD, pMVp35 and pMVp40 in 0.06 ml of phosphate buffered saline. Alternatively, in some embodiments in the examples below, the priming vaccines contained only the pMVgD, only the IL-12 plasmids, or wild-type HSV. The gD-containing plasmid and the IL-12 heterodimer-containing plasmids are preferably administered in a single composition intramuscularly (i.m.). However, alternatively, the plasmids may be co-administered sequentially or administered via a different route than that exemplified in the protocols below.

B. The Boosting Vaccines

The preferred boosting vaccines used in the experiments below were formulated to contain HSV type 2, strain 186 gD protein. The gD protein was produced in baculovirus and then purified as described in V. Landolfi et al, *Vaccine*, 11:407–414 (1993). Recombinant murine IL-12 heterodimeric protein was obtained from Genetics Institute, Inc., Cambridge, Mass. Alternatively, IL-12 protein can be prepared as described in U.S. Pat. No. 5,457,038, incorporated by reference herein. Preferably, suitable doses of gD protein and IL-12 protein were mixed together and immunized at a single site. Alternatively, the gD and IL-12 proteins may be co-administered sequentially or administered via different routes and sites than those exemplified in the protocols of Examples 2 and 3 below.

One embodiment f the boosting vaccine contained 50 pg gD protein/ml phosphate buffered saline (3 $\mu$g/dose), pH 7.4. Another embodiment of the boosting vaccine contained 50 $\mu$g gD protein/ml phosphate buffered saline (3 $\mu$g/dose), and 200 micrograms of aluminum phosphate (Wyeth-Lederle Vaccines) per dose. Still another embodiment of the boosting vaccine contained 50 $\mu$g gD protein/ml phosphate buffered saline (3 $\mu$g/dose), 200 micrograms of aluminum phosphate per dose, and 1 $\mu$g/dose of murine IL-12 protein [Genetics Institute, Inc.] in phosphate buffered saline, pH 7.4.

Example 2: Comparison of Vaccine Protocols

A. The Protocols

Fourteen groups (n=5/group) of seven-week old, female Balb/c mice (Charles River Laboratories) were utilized in this experiment. At day 0, the groups were administered with the following priming formulations:

Groups 1–5 were immunized on day 0 intramuscularly (i.m.) with the pMVgD plasmid described in Example 1 at a dose of 25 $\mu$gs and with the two IL-12 plasmids described above in Example 1 i.m. at a dose of 35 $\mu$gs/plasmid.

Groups 6–10 and 12 received no immunization on day 0.

Group 11 received just the two IL-12 plasmids described above in Example 1 i.m. at a dose of 35 $\mu$gs/plasmid on day 0.

Group 13 received 1×10$^5$ pfu of live, infectious wildtype HSV1 virus, NS strain (from Dr. H. Friedman, Children's Hospital of Philadelphia) in 0.03 ml volume via footpad injection on day 0.

Group 14 received 2×10$^3$ pfu of live, infectious wildtype HSV2, 186 strain, virus (American Type Culture Collection) administered in 0.03 ml volume via footpad injection on day 0.

After four weeks, the groups of animals received the following "boosts":

Groups 1 and 6 received a second administration (same dosage and route) of the gD2 and IL-12 containing plasmids.

Groups 2 and 7 received a second administration (same dosage and route) of the gD2 plasmid only.

Groups 3 and 8, however, received the second vaccine components. Full length gD2 protein, produced and isolated from baculovirus as described in Example 1, was administered i.m. at a dose of 3 $\mu$g and recombinant murine IL-12 (rmIL-12) heterodimeric protein in PBS was administered at a dose of 1 $\mu$g/dimer i.m. Groups 4 and 9 received only the full-length gD2 protein at a dose of 3 $\mu$g in PBS i.m.

Groups 5, 10, 13 and 14 received no second administration.

Group 11 received a second administration of IL-12 heterodimeric plasmids only at the same route and dosage as for the first administrations; and Group 12 received only the rmIL-12 at the same route and dose as above-specified.

At four weeks post the last immunization, blood was drawn, and spleens removed, from the animals and subjected to ELISA and lymphoproliferation assays, as described in York et al, *Vaccine*, 13:1706–1712 (1995). CTL assays were performed as described in York, cited above, with the following modifications: A20 cells were infected with HSV2 virus (M.O.I. 4 pfu/cell) for 4 hours at 37° C., 5% $CO_2$ and inactivated with UV light. These cells were employed as stimulator cells at a 1:20 ratio (HSV2 infected and UV inactivated A20 cells:spleen cells).

Additionally, a colorimetric serum microneutralization assay for HSV-1 and HSV2 using the commercial ELVIS™ HSV cell line [Biowhittaker, Inc.] was performed. Briefly this assay involved incubation of a predetermined amount of the virus with various dilutions of heat-inactivated serum samples or media only controls (virus controls) for 1 hour at 37° C., 5% $CO_2$, with or without guinea pig complement, followed by plating onto confluent monolayers of ELVIS HSV cells. After incubation under the same conditions, the monolayers were re-fed with ELVIS replacement medium and incubated for an additional 18 hours. The media was removed and 1.5% NP40-MEM (0.05 mls/well) was added and each microwell plate placed at –70° C. for at least 4 hours. After the lysates were thawed at 37° C., an equal volume of a β-galactosidase substrate was added and the plates were incubated at 37° C. for 40 minutes. The OD at 570 nm was determined. The neutralization titer was defined as the serum dilution that decreased the OD of the virus control by 50%.

Internal cytokine staining was performed, essentially according to She et al, *Intern'l. Immunol.*, 110:845–957 (1999), with the following modifications. Spleen cells were incubated at 37° C., 5% $CO_2$ for 3 days with heat-inactivated (56° C./30 minutes) HSV2 (10$^6$ pfu/2×10$^6$ spleen cells). The reference antigens were lymphocyte markers (CD3, CD4 or CD8), the activation antigen CD25, and the cytokine (IFN-γ or IL-10).

B. Results of the Assays

The humoral responses provided by the ELISA and Neutralization assay titers are illustrated in Table 1 below as geometric mean titers (GMT) of $IgG_1$, $IgG_2$ and Neut GMT, which is the geometric mean titer of serum neutralization activity. This is a logarithmic transformed expression of the capacity of test sera to neutralize viral infectivity in vitro. "Upper and lower 95% CI" are statistical expressions of variability of measurement encompassing the interval around the mean circumscribing the range within which 95% of observations should fall.

Briefly, maximal $IgG_1$ titers were achieved in sera derived from mice primed with gD and IL-12 plasmids, and boosted with unadjuvanted gD subunit. Elevation of $IgG_1$ titer also occurred in mice receiving a gD and IL-12 protein boost. The gD plasmid and IL-12 plasmid primed mice receiving gD subunit protein and IL-12 protein boost exhibited extremely high titers of $IgG_{2a}$ antibody. High titers of $IgG_{2a}$ were also seen in mice boosted with subunit gD alone. This observation suggests that plasmid priming of a Th1 dominant antibody response is maintained and augmented when boosted with subunit. Serum neutralization titers paralleled those of ELISA with very high titers seen in plasmid immunized mice boosted with subunit or with subunit gD and IL-12 protein.

Where groups of mice received gD subunit without adjuvant (i.e., a traditional formulation), the gD subunit, administered as described above, elicited high titers of $IgG_1$ ELISA antibody and moderate to high levels of serum neutralizing antibodies. The subunit formulated traditionally consistently failed to induce $IgG_{2a}$ ELISA antibodies or cell mediated (CMI) responses. In contrast, in the embodiment of the invention, co-formulation with IL-12 broadened the response to include $IgG_{2a}$ and CMI. This response profile (referred to as a Type 1 response profile) was maximized with DNA priming and subunit boost. See the results of Example 3 for comparison.

Statistical (ANOVA) analysis of serological data indicated that gD DNA and IL 12 DNA primed and gD/IL 12 subunit boosted group (Group 3) was clearly the best responding group within Example 2. This group also contained the second highest $IgG_1$ anti-gD serum titers and was statistically superior to all other groups, except for the gD DNA and IL 12 DNA primed and gD subunit boosted Group 4, in this respect. The gD DNA and IL 12 DNA primed and gD subunit boosted Group 4 was the second best responding group in terms of serum anti-HSV neutralizing and $IgG_{2a}$ anti-gD titers. The only difference between Group 4 and Group 3, the best responding group, was the absence of the IL-12 in the subunit boosting portion of the immunization regimen, which resulted in lower $IgG_{2a}$ anti-gD antibody titers and serum anti-HSV neutralizing titers. Statistical analysis of all neutralization titers with their corresponding $IgG_1$ or $IgG_{2a}$ anti-gD antibody titers indicated that a positive correlation (P=0.0001) existed between $IgG_{2a}$ anti-gD antibody titers with anti-HSV neutralizing activity, while no correlation was observed between $IgG_1$ titer and neutralizing titers.

TABLE 1A

ELISA $IgG_1$ Titers

| Group | Prime = wk 0 | Boost = wk 4 | $IgG_1$ GMT | Upper 95% CI | Lower 95% CI |
|---|---|---|---|---|---|
| 1 | gDDNA + IL12 DNA | gDDNA + IL12 DNA | 1161 | 9772 | 138 |
| 2 | gDDNA + IL12 DNA | gDDNA | 2004 | 23933 | 168 |
| 3 | gDDNA + IL12 DNA | gD subunit + IL12 protein | 14825 | 45082 | 4875 |
| 4 | gDDNA + IL12 DNA | gD subunit | 21627 | 78705 | 5943 |
| 5 | gDDNA + IL12 DNA | none | 916 | 13122 | 64 |
| 6 | none | gDDNA + IL12 DNA | 214 | 2917 | 16 |
| 7 | none | gDDNA | 3155 | 7145 | 1396 |
| 8 | none | gD subunit + IL12 protein | 6152 | 6982 | 5433 |
| 9 | none | gD subunit | 2786 | 3556 | 2183 |
| 10 | none | none | 25 | 25 | 25 |
| 11 | IL12 DNA | IL12 DNA | 25 | 25 | 25 |
| 12 | none | IL12 protein | 25 | 25 | 25 |
| 13 | HSV1 1 × $10^5$ pfu | none | 2518 | 10000 | 632 |
| 14 | HSV2 2 × $10^3$ pfu | none | 126 | 2388 | 7 |

TABLE 1B

ELISA $IgG_2$ Titers

| Group | Prime = wk 0 | Boost = wk 4 | IgG2a GMT | Upper 95% CI | Lower 95% CI |
|---|---|---|---|---|---|
| 1 | gDDNA + IL12 DNA | gDDNA + IL12 DNA | 6412 | 11298 | 3639 |
| 2 | gDDNA + IL12 DNA | gDDNA | 14125 | 42073 | 4742 |
| 3 | gDDNA + IL12 DNA | gD subunit + IL12 protein | 114551 | 199986 | 65615 |
| 4 | gDDNA + IL12 DNA | gD subunit | 65766 | 205116 | 21135 |
| 5 | gDDNA + IL12 DNA | none | 1213 | 18923 | 78 |
| 6 | none | gDDNA + IL12 DNA | 181 | 1824 | 18 |
| 7 | none | gDDNA | 2018 | 3614 | 1127 |
| 8 | none | gD subunit + IL12 protein | 3069 | 3890 | 2427 |
| 9 | none | gD subunit | 158 | 1337 | 19 |
| 10 | none | none | 25 | 25 | 25 |
| 11 | IL12 DNA | IL12 DNA | 25 | 25 | 25 |
| 12 | none | IL12 protein | 25 | 25 | 25 |
| 13 | HSV1 1 × $10^5$ pfu | none | 4285 | 5420 | 3388 |
| 14 | HSV2 2 × $10^3$ pfu | none | 14488 | 69502 | 3027 |

TABLE 1C

Neutralization Titers

| Group | Prime = wk 0 | Boost = wk 4 | Neut GMT | Upper 95% CI | Lower 95% CI |
|---|---|---|---|---|---|
| 1 | gDDNA + IL12 DNA | gDDNA + IL12 DNA | 70 | 398 | 12 |
| 2 | gDDNA + IL12 DNA | gDDNA | 243 | 1230 | 48 |
| 3 | gDDNA + IL12 DNA | gD subunit + IL12 protein | 2594 | 4256 | 1581 |
| 4 | gDDNA + IL12 DNA | gD subunit | 1236 | 21577 | 71 |
| 5 | gDDNA + IL12 DNA | none | 17 | 70 | 4 |
| 6 | none | gDDNA + IL12 DNA | 5 | 6 | 5 |
| 7 | none | gDDNA | 9 | 23 | 3 |
| 8 | none | gD subunit + IL12 protein | 35 | 101 | 12 |
| 9 | none | gD subunit | 5 | 5 | 5 |
| 10 | none | none | 5 | 5 | 5 |
| 11 | IL12 DNA | IL12 DNA | 5 | 5 | 5 |
| 12 | none | IL12 protein | 5 | 5 | 5 |
| 13 | HSV1 1 × $10^5$ pfu | none | 618 | 1358 | 281 |
| 14 | HSV2 2 × $10^3$ pfu | none | 145 | 205 | 103 |

The cellular responses of the lymphoproliferation assay results are illustrated in Table 2. This assay allowed for enumeration of antigen specific blastogenesis of immunocytes and served as a first level approximation of cellular responses. The assay involved the restimulation of spleen (or lymph node) cells for about 5 days in the presence of test antigen. The cells were then pulsed with tritiated thymidine and were then harvested and assayed for isotope uptake, a correlate of DNA synthesis and cellular division. The units of output from this assay were Counts per Minute (CPM), a direct correlate of isotope uptake. The CPM from control media were included in the table to demonstrate any non-specific activity seen in a given cell population (i.e., the HSV1 population had relatively high levels of background activity which might affect the apparent magnitude of response to test antigens).

Results are expressed as stimulation indices where the activity of spleen cells from mice administered a given immunogen restimulated with test antigen was divided by the activity of an "identical" cell population restimulated with controls, which included medium, Vero cell culture supernatant (sup.), or unrelated virus (A/Tx—an influenza strain). The significance of the Vero sup. was that all results should be about 1.0, no difference between control cell supernatant and medium restimulation. The columns of particular interest were those where cells were restimulated with gD, HSV1 or HSV2 (specific antigens). Consistent with humoral responses, maximal proliferative activity was observed in mice receiving gD and IL-12 plasmid priming vaccines with gD and IL-12 protein boosts.

TABLE 2

Lymphoproliferation

| Groups | Prime | Boost | gD | HSV1 | HSV2 | A/Tx | Vero Sup. | Medium (CPM) |
|---|---|---|---|---|---|---|---|---|
| 1 | gD DNA/IL12 DNA | gD DNA/IL12 DNA | 4.9 | 5.0 | 5.0 | 1.3 | 1.0 | 5540 |
| 2 | gD DNA/IL12 DNA | gD DNA | 4.0 | 4.0 | 3.2 | 1.4 | 0.9 | 3515 |
| 3 | gD DNA/IL12 DNA | gD/IL12 | 8.1 | 7.2 | 11.0 | 1.4 | 1.0 | 3576 |
| 4 | gD DNA/IL12 DNA | gD | 4.7 | 4.9 | 7.5 | 1.7 | 1.0 | 5744 |
| 5 | gD DNA/IL12 DNA | None | 3.0 | 4.1 | 4.5 | 1.4 | 0.9 | 5070 |
| 6 | None | gD DNA/IL12 DNA | 1.9 | 2.1 | 3.1 | 1.1 | 0.8 | 7551 |
| 7 | None | gD DNA | 2.9 | 3.4 | 4.1 | 1.6 | 0.7 | 3452 |
| 8 | None | gD/IL12 | 2.3 | 2.0 | 3.4 | 2.0 | 0.8 | 3873 |
| 9 | None | gD | 2.8 | 2.3 | 1.2 | 1.2 | 0.9 | 5780 |
| 10 | None | None | 0.6 | 1.5 | 1.7 | 1.3 | 0.8 | 4491 |
| 11 | IL12 DNA | IL12 DNA | 0.7 | 1.5 | 1.8 | 1.7 | 0.8 | 2491 |
| 12 | None | IL12 | 0.8 | 1.5 | 1.3 | 1.4 | 0.7 | 2802 |
| 13 | HSV1 | None | 0.9 | 4.6 | 3.4 | 0.8 | 0.9 | 20025 |
| 14 | HSV2 | None | 1.7 | 7.1 | 9.8 | 1.2 | 0.8 | 9050 |

The results from the Cm assays and internal cytokine staining assay are reported in FIG. 1 and Tables 3 and 4 below. No statistical analyses were performed on these data because a pooled sample without repeated measurements was used. However, one of skill in the art would find the relative elevation of the magnitude of response and the activity levels exhibited over a broad range of effector cell:target ratio to be indicative of positive results, as discussed below.

FIG. 1 illustrated in graphical form the CTL activity of Group 1 (gDpl12pl/(2)), Group 2 (gDpl12pl/gDpl), Group 3 (gDpl12pl/gDpr12pr), Group 4 (gDpl12pl/gDpr), Group 13 (live HSV1) and Group 14 (live HSV2). These groups all yielded perceptible CTL activity in contrast to the other groups. However, priming with gD and IL-12 plasmids followed by a gD subunit and IL-12 protein boost resulted in high levels of CTL activity, comparable at higher effector:target ratios with killing seen in virus control animals.

Tables 3 and 4 illustrate internal cytokine staining for interferon-γ and Interleukin 4. Internal cytokine data related to the relative frequency of cells simultaneously bearing specific phenotypic markers (CD3=pan-T cell; CD4=helper T cell; CD8=cytotoxic T cell), a marker of cellular activation (CD25) and the internal expression of interferon gamma (IFN-γ a correlate of a Type 1 response) or IL-4 (a correlate of a Type 2 response). These assays were performed to better define the activation state and phenotype of cytokine secreting cells attributable to an immunization regimen, and served as corroborative data for CTL results of FIG. 1. The references in the antigen column (Ag) are heat inactivated HSV2 virus (HSV2) and HSV infected A20 cells (A20). Coordinate staining for internal IFN-γ, CD4 or CD co-receptor and CD24 T-cell activation marker suggested that immunization with gD DNA and IL-12 DNA followed by gD subunit and IL-12 protein boost engendered elevated levels of IFN-γ producing cells. These were observed at levels comparable to virus controls and followed a similar pattern, characterized by a CD4+ phenotypic profile. Little, if any, IL-4 activity was detected for any treatment group. In general, about a 2-fold increase in the frequency of cells, relative to controls, is suggestive of a biologically relevant alteration.

TABLE 3

Internal Cytokine Staining of Activated Lymphocyte Populations for IFNγ

| | | | | % Staining | | |
|---|---|---|---|---|---|---|
| Group | Prime | Boost | Antigen | CD3/IFNγ/CD25 | CD4/IFNγ/CD25 | CD8/IFNγ/CD25 |
| 1 | gD DNA/IL12 DNA | gD DNA/IL12 DNA | HSV2 | 13.9 | 14.0 | 9.3 |
| 2 | gD DNA/IL12 DNA | gD DNA | HSV2 | 11.1 | 11.7 | 7.5 |
| 3 | gD DNA/IL12 DNA | gD/IL12 | HSV2 | 17.3 | 24.7 | 7.9 |
| 4 | gD DNA/IL12 DNA | gD | HSV2 | 10.9 | 13.9 | 5.7 |
| 5 | gD DNA/IL12 DNA | None | HSV2 | 9.5 | 14.2 | 6.2 |
| 6 | None | gD DNA/IL12 DNA | HSV2 | 10.0 | 7.9 | 6.0 |
| 7 | None | gD DNA | HSV2 | 8.2 | 11.8 | 6.8 |
| 8 | None | gD/IL12 | HSV2 | 5.7 | 7.6 | 9.8 |
| 9 | None | gD | HSV2 | 2.0 | 1.3 | 5.3 |
| 10 | None | None | HSV2 | 4.1 | 3.5 | 7.0 |
| 11 | IL12 DNA | IL12 DNA | HSV2 | 2.8 | 3.0 | 8.2 |
| 12 | None | IL12 | HSV2 | 2.3 | 2.2 | 6.1 |
| 13 | HSV1 | None | HSV2 | 16.6 | 19.5 | 7.2 |
| 14 | HSV2 | None | HSV2 | 22.6 | 27.5 | 9.8 |
| 3a | gD DNA/IL12 DNA | gD/IL12 | A20 | 17.3 | 25.6 | 5.0 |
| Control | HSV1 | None | A20 | 16.4 | 20.5 | 6.5 |
| Control | None | None | A20 | 6.5 | 9.4 | 3.2 |

TABLE 4

Internal Cytokine Staining of Activated Lymphocyte Populations for IL-4

| | | | | % Staining | | |
|---|---|---|---|---|---|---|
| Group | Prime | Boost | Antigen | CD3/IFNγ/CD25 | CD4/IFNγ/CD25 | CD8/IFNγ/CD25 |
| 1 | gD DNA/IL12 DNA | gD DNA/IL12 DNA | HSV2 | 1.5 | 2.7 | 2.1 |
| 2 | gD DNA/IL12 DNA | gD DNA | HSV2 | 1.3 | 3.0 | 3.4 |
| 3 | gD DNA/IL12 DNA | gD/IL12 | HSV2 | 2.0 | 1.7 | 2.7 |
| 4 | gD DNA/IL12 DNA | gD | HSV2 | 1.9 | 3.4 | 1.1 |
| 5 | gD DNA/IL12 DNA | None | HSV2 | 1.5 | 2.4 | 3.2 |
| 6 | None | gD DNA/IL12 DNA | HSV2 | 1.5 | 2.4 | 1.9 |
| 7 | None | gD DNA | HSV2 | 1.1 | 1.8 | 3.7 |
| 8 | None | gD/IL12 | HSV2 | 1.8 | 3.1 | 3.6 |
| 9 | None | gD | HSV2 | 1.6 | 2.2 | 3.3 |
| 10 | None | None | HSV2 | 0.5 | 2.1 | 1.5 |
| 11 | IL12 DNA | IL12 DNA | HSV2 | 0.9 | 1.7 | 2.4 |
| 12 | None | IL12 | HSV2 | 0.7 | 1.6 | 2.0 |
| 13 | HSV1 | None | HSV2 | 0.6 | 0.2 | 1.8 |
| 14 | HSV2 | None | HSV2 | 0.2 | 1.6 | 0.2 |
| 3a | gD DNA/IL12 DNA | gD/IL12 | A20 | 0.1 | 0.6 | 0.5 |
| Control | HSV1 | None | A20 | 0.8 | 0.4 | 0.0 |
| Control | None | None | A20 | 0.0 | nd | nd |

Example 3:

Comparison of Vaccine Protocols

A. The Protocols

Fifteen groups (n=5/group) of Balb/C mice were utilized in this experiment. Groups 1–5 were immunized on day 0 intramuscularly (i.m.) with the pMVgD plasmid described in Example 1 at a dose of 25 μgs and with the two IL-12 plasmids described above in Example 1 i.m. at a dose of 35 μgs/plasmid. Groups 6–7 received just the two IL-12 plasmids described above in Example 1 i.m. at a dose of 35 gs/plasmid on day 0. Groups 8–15 received no immunization at day 0.

After four weeks, the groups of animals received the following "boosts": Groups 1–5 received a repeated administrated using the same dosages and route of the gD2 and IL-12 plasmids. Groups 6–7 also received a repeated dosage of their first priming composition. Group 8 received $1 \times 10^5$ pfu of live, infectious wildtype HSV1 strain NS virus administered in 0.03 ml/volume via footpad injection. Group 9 received $2 \times 10^3$ pfu of live, infectious wildtype HSV2, strain 186 virus administered in 0.03 ml/volume via footpad injection. Group 10 received no administration at four weeks. Group 11 received full length gD2 protein, administered i.m. at a dose of 3 μg. Group 12 received i.m. the full length gD2 protein (3 μg/dose) adjuvanted with 200 μg/dose aluminum phosphate. Group 13 received the full length gD2 protein at a dose of 3 μg and rmIL-12 heterodimeric protein in PBS administered i.m. at a dose of 1 μg/dimer mixed together in PBS and administered i.m. Group 14 received the gD2 protein (0.3 μg/dose) adjuvanted with aluminum phosphate and the mIL-12 protein heterodimeric protein (1.0 μg/dose) mixed together in PBS and administered i.m. Group 15 received just mIL-12 protein i.m. at 1 μg/dimer.

At the eight week timepoint, the same groups of experimental animals were treated as follows:

Groups 1 and 8–10 received nothing. Group 2 received a third dose of the gD2/IL-12 plasmids that comprised the first and second doses. Group 3 received another dose of the gD plasmid only. Groups 4 and 13 received the full length gD2 protein administered i.m. at a dose of 3 μg, and rmIL-12 heterodimeric protein administered at a dose of 1 μg/dimer mixed together in PBS and administered i.m. Groups 5 and 11 received only the full-length gD2 subunit. Group 6 received only the IL-12 plasmids. Group 7 received only the IL-12 protein. Group 12 received a second dose of the alum-adjuvanted gD subunit. Group 14 received a second dose of the alum-adjuvanted gD subunit with the mIL-12 heterodimeric proteins. Group 15 received a second dose of the mIL-12 heterodimeric proteins only.

At week 12, blood was drawn from the animals and subjected to ELISA, neutralization and lymphoproliferation assays described in Example 2 above.

B. Results of the Assays

The ELISA and Neutralization assay titers for the groups in this experiment are illustrated in Table 5 below. The results of this experiment contrasted with the results of Example 2 above. The contrast is most notable in the group receiving two immunizations of gD and IL-12 plasmid followed by an unadjuvanted gD subunit boost (Group 3). The ELISA and neutralizing titers were not significantly different from those induced by two doses of gD plasmids and IL-12 plasmids without protein boosting. This type of observation has previously been seen with repeated immunization using gD and IL-12 plasmids. In contrast, two immunizations with gD and IL-12 plasmids, followed by a gD and IL-12 protein boost (Group 4) resulted in extremely high $IgG_{2a}$ ELISA and neutralization titers even when compared with two inocula of aluminum phosphate-adjuvanted subunit gD formulated with IL-12 protein (Group 14). See the discussion under Table 1.

Statistical (ANOVA) analysis of serological data indicated that Group 4, that received two immunizations with gD DNA and IL-12 DNA and was boosted with gD/IL-12 protein, was far superior to all other groups with respect to greatest serum anti-HSV neutralizing and $IgG_{2a}$ anti-gD titers.

TABLE 5A

ELISA $IgG_1$ Titers

| Group | Prime = wk 0 | 1st Boost = wk 4 | 2nd Boost = wk 8 | IgG1 GMT | Upper 95% CI | Lower 95% CI |
|---|---|---|---|---|---|---|
| 1 | gDDNA + IL12 DNA | gDDNA + IL12 DNA | none | 2636 | 9419 | 736 |
| 2 | gDDNA + IL12 DNA | gDDNA + IL12 DNA | gDDNA + IL12 DNA | 2851 | 21979 | 370 |
| 3 | gDDNA + IL12 DNA | gDDNA + IL12 DNA | gDDNA | 1374 | 7780 | 243 |
| 4 | gDDNA + IL12 DNA | gDDNA + IL12 DNA | gD subunit + 12 protein | 4395 | 5395 | 3589 |
| 5 | gDDNA + IL12 DNA | gDDNA + IL12 DNA | gD subunit | 2173 | 3311 | 1426 |
| 6 | IL12 DNA | IL12 DNA | IL12 DNA | 101 | 161 | 64 |
| 7 | IL12 DNA | IL12 DNA | IL12 protein | 94 | 139 | 64 |
| 8 | none | HSV1 $1 \times 10^5$ pfu | none | 499 | 2323 | 107 |
| 9 | none | HSV2 $2 \times 10^3$ pfu | none | 769 | 1710 | 347 |
| 10 | none | none | none | 70 | 126 | 39 |
| 11 | none | gD subunit | gD subunit | 5572 | 7079 | 4375 |
| 12 | none | gD/AlPO$_4$ | gD/AlPO$_4$ | 58479 | 122462 | 27990 |
| 13 | none | gD + IL12 | gD + IL12 | 9162 | 11668 | 7194 |
| 14 | none | gD/AlPO$_4$ + IL12 | gD/AlPO$_4$ + IL12 | 12162 | 16181 | 9120 |
| 15 | none | IL12 | IL12 | 99 | 416 | 24 |

TABLE 5B

ELISA IgG$_2$ Titers

| Group | Prime = wk 0 | 1$^{st}$ Boost = wk 4 | 2$^{nd}$ Boost = wk 8 | IgG1 GMT | Upper 95% CI | Lower 95% CI |
|---|---|---|---|---|---|---|
| 1 | gDDNA + IL12 DNA | gDDNA + IL12 DNA | none | 2642 | 4775 | 1462 |
| 2 | gDDNA + IL12 DNA | gDDNA + IL12 DNA | gDDNA + IL12 DNA | 2399 | 3162 | 1824 |
| 3 | gDDNA + IL12 DNA | gDDNA + IL12 DNA | gDDNA | 3548 | 7745 | 1626 |
| 4 | gDDNA + IL12 DNA | gDDNA + IL12 DNA | gD subunit + 12 protein | 92045 | 121619 | 69823 |
| 5 | gDDNA + IL12 DNA | gDDNA + IL12 DNA | gD subunit | 3899 | 18793 | 809 |
| 6 | IL12 DNA | IL12 DNA | IL12 DNA | 73 | 249 | 21 |
| 7 | IL12 DNA | IL12 DNA | IL12 protein | 25 | 25 | 25 |
| 8 | none | HSV1 1 × 10$^5$ pfu | none | 3155 | 56494 | 176 |
| 9 | none | HSV2 2 × 10$^3$ pfu | none | 1986 | 7211 | 547 |
| 10 | none | none | none | 47 | 97 | 23 |
| 11 | none | gD subunit | gD subunit | 44 | 115 | 17 |
| 12 | none | gD/AlPO$_4$ | gD/AlPO$_4$ | 78 | 312 | 19 |
| 13 | none | gD + IL12 | gD + IL12 | 2891 | 4667 | 1795 |
| 14 | none | gD/AlPO$_4$ + IL12 | gD/AlPO$_4$ + IL12 | 22387 | 39355 | 12764 |
| 15 | none | IL12 | IL12 | 40 | 93 | 17 |

TABLE 5C

Neutralization Titers

| Group | Prime = wk 0 | 1$^{st}$ Boost = wk 4 | 2$^{nd}$ Boost = wk 8 | Neut GMT | Upper 95% CI | Lower 95% CI |
|---|---|---|---|---|---|---|
| 1 | gDDNA + IL12 DNA | gDDNA + IL12 DNA | none | 21 | 105 | 4 |
| 2 | gDDNA + IL12 DNA | gDDNA + IL12 DNA | gDDNA + IL12 DNA | 80 | 473 | 14 |
| 3 | gDDNA + IL12 DNA | gDDNA + IL12 DNA | gDDNA | 102 | 242 | 43 |
| 4 | gDDNA + IL12 DNA | gDDNA + IL12 DNA | gD subunit + 12 protein | 4955 | 9162 | 2679 |
| 5 | gDDNA + IL12 DNA | gDDNA + IL12 DNA | gD subunit | 266 | 1919 | 37 |
| 6 | IL12 DNA | IL12 DNA | IL12 DNA | 5 | 5 | 5 |
| 7 | IL12 DNA | IL12 DNA | IL12 protein | 5 | 5 | 5 |
| 8 | none | HSV1 1 × 10$^5$ pfu | none | 708 | 1462 | 344 |
| 9 | none | HSV2 2 × 10$^3$ pfu | none | 136 | 617 | 30 |
| 10 | none | none | none | 5 | 5 | 5 |
| 11 | none | gD subunit | gD subunit | 163 | 558 | 48 |
| 12 | none | gD/AlPO$_4$ | gD/AlPO$_4$ | 365 | 1778 | 75 |
| 13 | none | gD + IL12 | gD + IL12 | 875 | 3133 | 244 |
| 14 | none | gD/AlPO$_4$ + IL12 | gD/AlPO$_4$ + IL12 | 2037 | 3199 | 1297 |
| 15 | none | IL12 | IL12 | 5 | 5 | 5 |

The lymphoproliferation assay results of the same groups are illustrated in Table 6. These responses were similar to those of the groups in Example 2. However, following the additional immunization, Groups 2, 3, 4, and 5, which all received 3 immunizations with gD vaccines, evidenced lymphoproliferative responses greater than group 14 stimulation indices. This relates to the effect of the mixed regimen prime/boost when compared with the traditional subunit/ AlPO$_4$ immunization scheme.

TABLE 6

Lymphoproliferation

| Groups | Prime | Boost-1 | Boost-2 | gD | HSV1 | HSV2 | A/Tx | Vero Sup. | Medium (CPM) |
|---|---|---|---|---|---|---|---|---|---|
| 1 | gDDNA/ IL12 DNA | gDDNA/ IL12 DNA | none | 7.0 | 1.6 | 3.8 | 1.1 | 1.0 | 3187 |
| 2 | gDDNA/ IL12 DNA | gD DNA/ IL12 DNA | gDDNA/ IL12 DNA | 14.1 | 3.1 | 7.0 | 2.2 | 0.8 | 1165 |
| 3 | gDDNA/ IL12 DNA | gDDNA/ IL12 DNA | gDDNA | 16.9 | 5.1 | 10.4 | 3.5 | 1.7 | 1431 |
| 4 | gDDNA/ IL12 DNA | gDDNA/ IL12 DNA | gD/IL12 | 31.6 | 5.7 | 12.7 | 2.0 | 0.7 | 2119 |
| 5 | gDDNA/ IL12 DNA | gDDNA/ IL12 DNA | gD | 23.3 | 3.2 | 9.5 | 1.8 | 1.5 | 2543 |
| 6 | IL12 DNA | IL12 DNA | IL12 DNA | 0.5 | 1.8 | 3.0 | 2.5 | 1.5 | 1306 |
| 7 | IL12 DNA | IL12 DNA | IL12 | 1.7 | 2.5 | 3.8 | 3.6 | 2.5 | 1153 |
| 8 | None | HSV1 | None | 1.5 | 4.1 | 4.6 | 1.6 | 1.5 | 9688 |
| 9 | None | HSV2 | None | 5.2 | 10.4 | 25.3 | 2.7 | 2.3 | 2485 |
| 10 | None | None | None | 2.4 | 2.0 | 4.1 | 4.5 | 1.7 | 1082 |
| 11 | None | gD | gD | 11.0 | 1.9 | 2.9 | 2.1 | 1.0 | 2793 |
| 12 | None | gD/AlPO$_4$ | gD/AlPO$_4$ | 10.8 | 2.4 | 4.1 | 2.8 | 1.7 | 2280 |
| 13 | None | gD/IL12 | gD/IL12 | 6.7 | 1.8 | 5.3 | 2.2 | 3.3 | 8126 |
| 14 | None | gD/AlPO$_4$/ IL12 | gD/AlPO$_4$/ IL12 | 4.5 | 2.2 | 4.6 | 1.5 | 1.1 | 4854 |
| 15 | None | IL12 | IL12 | 1.9 | 1.0 | 1.9 | 1.4 | 1.1 | 4734 |

The CTL activity for these groups is illustrated in Table 7. Enumeration of CTL activity for these experimental groups included a whole population analysis as well as selective depletion of CD4+ or CD8+ cells. Table 7 indicates that peak activity occurred in cells derived from mice immunized twice with gD and IL-12 plasmid, and boosted with gD subunit and IL-12 protein. Depletion analysis denoted that the cytolysis was almost exclusively attributable to the CD4+ populations in all groups except the HSV2 controls, in which a mixed phenotype was seen. The abbreviation "nd" means not done.

The biological significance of these data resides in the relative elevation of activity ascribed to the mixed regimen prime-boost animals when compared with traditional treatments. Further, the fact that in the Balb/C mouse model virtually all CTL activity segregates with the CD4+ cell population correlates closely with the internal cytokine data described above. Thus, the prime-boost regimen results in treatment related increases in the frequency of CD4/CD25/ IFNγ cells.

TABLE 7A

CTL Activity

| Prime | Boost #1 | Boost #2 | | Effector: Target Ratio | | | | | | |
|---|---|---|---|---|---|---|---|---|---|---|
| | | | | 50 | 25 | 12.5 | 6.25 | 3.125 | 1.5 | 0.75 |
| gDDNA + IL12 DNA | gDDNA + IL12 DNA | None | undepleted | 19.8 | 16.8 | 15.8 | 12.7 | 8.9 | 5.6 | 1.7 |
| | | | CD4 depleted | 0 | 0 | 0 | 0 | 0 | 0.2 | 0 |
| | | | CD8 depleted | 19 | 16 | 11 | 9.5 | 9 | 7.4 | 12.4 |
| gDDNA + IL12 DNA | gDDNA + IL12 DNA | gDDNA + IL12 DNA | undepleted | 15.3 | 16.9 | 13.2 | 13.9 | 11.5 | 8.3 | 1.7 |
| | | | CD4 depleted | 0 | 0 | 0 | 0 | 0 | 0 | 0 |
| | | | CD8 depleted | 18 | 17.6 | 14.3 | 6 | 4.4 | 5.1 | 1.5 |
| gDDNA + | gDDNA + | gDDNA | undepleted | 12.8 | 16.4 | 14.4 | 11 | 11.2 | 9.1 | 4.6 |

TABLE 7A-continued

CTL Activity

| Prime | Boost #1 | Boost #2 | | Effector: Target Ratio | | | | | | |
|---|---|---|---|---|---|---|---|---|---|---|
| | | | | 50 | 25 | 12.5 | 6.25 | 3.125 | 1.5 | 0.75 |
| IL12 DNA | IL12 DNA | | CD4 depleted | 0 | 2.4 | 0 | 0 | 0 | 0 | |
| | | | CD8 depleted | 15.2 | 13 | 10 | 6.5 | 2 | 3.8 | 0 |
| gDDNA + IL12 DNA | gDDNA + IL12 DNA | gD subunit IL12 protein | undepleted | 33.9 | 27.4 | 25.1 | 18 | 16.5 | 15 | 6.5 |
| | | | CD4 depleted | 0 | 0 | 0 | 0 | 0 | 0 | 1.9 |
| | | | CD8 depleted | 43.8 | 42.6 | 39.4 | 24.9 | 17.7 | 10 | 1.6 |
| gDDNA + IL12 DNA | gDDNA + IL12 DNA | gD subunit | undepleted | 4 | 5.5 | 4.6 | 5.9 | 2.7 | 0 | 0 |
| | | | CD4 depleted | 0 | 3.4 | 5 | 6.4 | 4.8 | 2.5 | 2.7 |
| | | | CD8 depleted | 19.1 | 14.7 | 10 | 11.2 | 3.6 | 3.3 | 1.3 |
| IL12 DNA | IL12 DNA | IL12 DNA | undepleted | 4.9 | 5 | 4.7 | 1.3 | 2.3 | 1.7 | 0 |
| | | | CD4 depleted | nd | nd | nd | nd | nd | nd | nd |
| | | | CD8 depleted | nd | nd | nd | nd | nd | nd | nd |
| IL12 DNA | IL12 DNA | IL12 protein | undepleted | 2.4 | 3.5 | 8.4 | 0.4 | 1.1 | 0.4 | 0.1 |
| | | | CD4 depleted | 0.9 | 2.5 | 2.7 | 4.3 | 3.5 | 1.3 | 0.5 |
| | | | CD8 depleted | 8.9 | 7.7 | 8.6 | 7.9 | 9.7 | 8 | 3.7 |

TABLE 7B

CTL Activity

| Prime | Boost #1 | Boost #2 | | Effector: Target Ratio | | | | | | |
|---|---|---|---|---|---|---|---|---|---|---|
| | | | | 50 | 25 | 12.5 | 6.25 | 3.125 | 1.5 | 0.75 |
| none | HSV1 | none | undepleted | 34.5 | 32.6 | 43.6 | 32.3 | 21.1 | 11.2 | 7.7 |
| | | | CD4 depleted | nd | nd | nd | nd | nd | nd | nd |
| | | | CD8 depleted | nd | nd | nd | nd | nd | nd | nd |
| none | HSV2 | none | undepleted | 42.2 | 38.1 | 36.7 | 34.9 | 22 | 18.7 | 11.9 |
| | | | CD4 depleted | 37.8 | 29.1 | 29.7 | 24.4 | 16.3 | 13.4 | 8.6 |
| | | | CD8 depleted | 25.3 | 22.7 | 15.7 | 13.2 | 12.7 | 9.1 | 0 |
| none | none | none | undepleted | 4.8 | 7.4 | 0.1 | 8.9 | 6.6 | 4 | 0.2 |
| | | | CD4 depleted | 0.6 | 0.4 | 1.4 | 2.9 | 3.5 | 2.7 | 5 |
| | | | CDS depleted | 9.2 | 6.8 | 6.2 | 2.8 | 5.2 | 5 | 0 |
| none | gD subunit | gD subunit | undepleted | 6.6 | 8.1 | 9.2 | 7.8 | 5.1 | 4.6 | 3.1 |
| | | | CD4 depleted | nd | nd | nd | nd | nd | nd | nd |
| | | | CD8 depleted | nd | nd | nd | nd | nd | nd | nd |
| none | gD-AlPO$_4$ | gD-AlPO$_4$ | undepleted | 6.1 | 4.9 | 4.7 | 9.3 | 0 | 0 | 0 |
| | | | CD4 depleted | nd | nd | nd | nd | nd | nd | nd |
| | | | CD8 depleted | nd | nd | nd | nd | nd | nd | nd |
| none | gD subunit IL12 protein | gD subunit IL12 protein | undepleted | 22.1 | 17.8 | 13.7 | 10.5 | 2.5 | 0.2 | 0 |
| | | | CD4 depleted | 0 | 0 | 0 | 0 | 0 | 0 | 0 |
| | | | CD8 depleted | 21.4 | 15.8 | 13.3 | 7.8 | 3.8 | 8.7 | 5.5 |
| none | gD/AlPO$_4$ + IL12 protein | gD/AlPO$_4$ + IL12 protein | undepleted | 0 | 1.9 | 7 | 2.4 | 3.1 | 1.4 | 1.5 |
| | | | CD4 depleted | 0 | 0 | 0 | 0 | 0 | 0 | 0 |
| | | | CD8 depleted | 10.3 | 11.3 | 9 | 8.6 | 6.9 | 6.3 | 0.4 |
| none | IL12 protein | IL12 protein | undepleted | 0.7 | 1.8 | 4.9 | 5.9 | 5.8 | 0 | 0.5 |
| | | | CD4depleted | nd | nd | nd | nd | nd | nd | nd |
| | | | CD8 depleted | nd | nd | nd | nd | nd | nd | nd |

The results described above for Examples 2 and 3 indicate an advantage of a prime-boost regimen for an HSV vaccine protocol, in which plasmids expressing the gD2 gene and the IL-12 cytokine are used to prime an immune response, followed by a boosting formulation which consists of a gD2 subunit and the IL-12 proteins. This regimen appears to prime a dominant Th1 profile of response, which is significantly augmented by protein boost. Moreover the qualitative and quantitative effects of this type of regimen on both humoral and cellular responses are enhanced.

The attractiveness of formulation of HSV gD subunit vaccine with IL-12 resides in the capacity of this cytokine to modulate a shift in the response profile, typically associated with subunit vaccines, from a Type 2 dominant response (characterized by the presence of IL-4, IL-5, IL-10 and the primary induction of humoral responses) to a Type 1 dominant profile (with high levels of IL-2 and IFN-γ, associated with induction of cellular responses as well as complement fixing IgG subtypes). The Type 1 response profile has been closely associated with protective immunity to a number of intracellular pathogens and is considered to be an important element in a therapeutic indication for HSV infection. The present invention harnesses the capacity of DNA (HSV gD antigen+IL-12) to effectively prime the immune system which is then boosted significantly by administration of protein HSV gD glycoprotein and IL-12.

The disclosures of each and every patent, patent application, and publication cited herein are hereby incorporated herein by reference in their entirety. While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inducing an immune response in a mammal to a Herpes Simplex Virus pathogen comprising the steps of:
   (a) at least one immunization with an effective amount of a DNA composition which comprises:
      (i) a first nucleic acid molecule comprising a DNA sequence encoding HSV type 1 or type 2 gD protein; and
      (ii) a second nucleic acid molecule comprising a DNA sequence encoding each Interlukin-12 (IL-12) heterodimer subunit; and
   (b) at least one subsequent immunization with an effective amount of a protein composition which comprises:
      (i) the HSV type 1 or type 2 gD protein; and
      (ii) the IL-12 heterodimer.

2. The method according to claim 1, wherein there are two immunizations with the DNA composition of step (a).

3. The method according to claim 1, wherein said DNA composition further comprises a local anesthetic in an amount that forms a complex with said nucleic acid molecules (i) and (ii).

4. The method according to 1 wherein said DNA sequence encoding the HSV gD protein in step (a)(i) is a DNA sequence encoding the HSV type 2 gD protein and wherein said HSV gD protein in step (b)(i) is the HSV type 2 gD protein.

5. The method according to 1 wherein said DNA sequence encoding the HSV gD protein in step (a)(i) is a DNA sequence encoding the HSV type 1 gD protein and wherein said HSV gD protein in step (b)(i) is the HSV type 1 gD protein.

6. The method according to claim 1 wherein said second nucleic acid molecule comprises a first plasmid comprising a DNA sequence encoding the IL-12 p35 sequence operably linked to a suitable promoter which directs expression of said p35 protein in a mammalian cell, and a second plasmid comprising a DNA sequence encoding the IL-12 p40 protein in a mammalian cell.

7. The method according to claim 1, wherein said first nucleic acid molecules comprises said gD-encoding DNA sequence operably linked to a suitable promoter which directs expression of said gD protein in a mammalian cell.

8. The method according to claim 3 wherein said complex is between about 50 to about 150 nm in diameter.

9. The method according to claim 3 wherein said local anesthetic is bupivicaine.

10. The method according to claim 3 wherein said DNA composition further comprises one or more compounds selected from the group consisting of cationic lipids, neutral lipids, anionic lipids, cationic surfactants, neutral surfactants, anionic surfactants, cationic detergents, neutral detergents and anionic detergents.

11. The methods according to claim 1 wherein said IL-12 heterodimer subunits comprise the p35 subunit and the p40 subunit.

12. The method according to claim 1, wherein said DNA composition is administered 2–32 weeks before administering said protein vaccine.

* * * * *

UNITED STATES PATENT AND TRADEMARK OFFICE
CERTIFICATE OF CORRECTION

PATENT NO. : 6,867,000 B2
DATED : March 15, 2005
INVENTOR(S) : Eric M. Mishkin et al.

It is certified that error appears in the above-identified patent and that said Letters Patent is hereby corrected as shown below:

Title page,
Item [54], Title, after "METHOD OF ENHANCING IMMUNE RESPONSES TO HERPES" insert -- SIMPLEX VIRUS VACCINE --.

Signed and Sealed this

Thirteenth Day of September, 2005

JON W. DUDAS
*Director of the United States Patent and Trademark Office*